(12) United States Patent
Yokota

(10) Patent No.: US 9,115,985 B2
(45) Date of Patent: Aug. 25, 2015

(54) INNER SURFACE SHAPE MEASURING APPARATUS

(71) Applicant: OLYMPUS CORPORATION, Shibuya-ku, Tokyo (JP)

(72) Inventor: Masayoshi Yokota, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/166,671

(22) Filed: Jan. 28, 2014

(65) Prior Publication Data

US 2014/0211212 A1 Jul. 31, 2014

(30) Foreign Application Priority Data

Jan. 31, 2013 (JP) ................. 2013-016611

(51) Int. Cl.
*G01B 11/24* (2006.01)
*G01B 11/25* (2006.01)
*G02B 23/24* (2006.01)

(52) U.S. Cl.
CPC ............ *G01B 11/25* (2013.01); *G01B 11/2518* (2013.01); *G02B 23/24* (2013.01)

(58) Field of Classification Search
USPC ................. 356/237.1–237.6, 241.1–241.6, 356/601–606
See application file for complete search history.

(56) References Cited

U.S. PATENT DOCUMENTS 8,049,901 B2 * 11/2011 Aoki et al. ................ 356/601
2011/0001984 A1 * 1/2011 Keller et al. .............. 356/612

FOREIGN PATENT DOCUMENTS

JP 2862715 B2 3/1999

* cited by examiner

*Primary Examiner* — Tri T Ton
(74) *Attorney, Agent, or Firm* — Holtz, Holtz, Goodman & Chick PC

(57) ABSTRACT

An inner surface shape measuring apparatus that measures an inner surface shape of a tested object by using a light-section method includes: a projection section which includes an outer peripheral section having a tubular shape and having a slit that light is capable of penetrating and that is provided in a circumferential direction, and a light source unit having a light-emitting element and arranged in the outer peripheral section, the projection section projecting a luminous flux that has a predetermined thickness from the slit onto the tested object; and an imaging section which images the inner surface of the tested object with the luminous flux projected thereon.

12 Claims, 4 Drawing Sheets

INNER SURFACE SHAPE MEASURING APPARATUS

BACKGROUND OF THE INVENTION

1. Field of the Invention

The present invention relates to an inner surface shape measuring apparatus and more specifically to an inner surface shape measuring apparatus which performs measurement by using a light-section method.

Priority is claimed on Japanese Patent Application No. 2013-016611, filed Jan. 31, 2013, the contents of which are incorporated herein by reference.

2. Description of Related Art

Conventionally, for the purpose of measuring the inner surface shape of a tested object, an inner surface shape measuring apparatus that performs measurement by using a light-section method has been used. For example, a radially spreading planar luminous flux is projected toward the entire circumference of the peripheral wall surface of a tested object having a tubular internal space, whereby a ring-shaped light-section line is produced over a circumferential direction on the peripheral wall surface. An apparatus is known in which it is possible to seek the inner surface shape of a tested object in a predetermined coordinate system by detecting the position of a light-section line on an image obtained by imaging the light-section line.

In Japanese Patent No. 2862715, there is described a planar luminous flux projecting apparatus for light-section measurement (hereinafter simply referred to as a "light projecting apparatus") used to perform such inner surface shape measurement. The light projecting apparatus includes a light source, an optical device which makes a luminous flux from the light source direct forward, and a conical reflecting minor which performs direction conversion of the luminous flux, thereby projecting the luminous flux as a radially spreading planar luminous flux.

SUMMARY OF THE INVENTION

According to a first aspect of the invention, an inner surface shape measuring apparatus that measures an inner surface shape of a tested object by using a light-section method, includes: a projection section which includes an outer peripheral section having a tubular shape and having a slit that light is capable of penetrating and that is provided in a circumferential direction, and a light source unit having a light-emitting element and arranged in the outer peripheral section, the projection section projecting a luminous flux that has a predetermined thickness from the slit onto the tested object; and an imaging section which images the inner surface of the tested object with the luminous flux projected thereon.

According to a second aspect of the present invention, in the first aspect, the outer peripheral section may have a tubular main body having a transparency, and a shielding section which is mounted so as to be slidable with respect to the main body and at least a portion of which has a light shielding property.

According to a third aspect of the present invention, in the second aspect, the shielding section may be configured with a plurality of shielding tubes having a light shielding property.

According to a fourth aspect of the present invention, in the first aspect, at least a portion of the outer peripheral section may have a light shielding property and the light source unit may be mounted so as to be slidable with respect to the outer peripheral section.

According to a fifth aspect of the present invention, in any one of the first to fourth aspects, a plurality of light-emitting elements may be arranged side by side in a circumferential direction of the projection section in the outer peripheral section.

According to a sixth aspect of the present invention, in any one of the first to fourth aspects, the light-emitting element may be arranged on a central axis of the projection section such that a light-emitting surface of the light-emitting element faces the tip end side of the outer peripheral section.

According to a seventh aspect of the present invention, an inner surface shape measuring apparatus that measures an inner surface shape of a tested object by using a light-section method, includes: a projection section which includes an outer peripheral section that is a tubular shape and has a light shielding area that blocks light and is provided in a circumferential direction, and a light source unit having one or more light-emitting elements and arranged in the outer peripheral section, and the projection section projecting a shadow that has a predetermined thickness onto the tested object; and an imaging section which images the inner surface of the tested object with the shadow projected thereon.

According to an eighth aspect of the present invention, in the seventh aspect, the outer peripheral section may have a tubular main body having a transparency, and the light shielding area may be mounted so as to be slidable with respect to the main body.

According to a ninth aspect of the present invention, in the eighth aspect, the light shielding area may be configured with a plurality of shielding tubes having a light shielding property.

According to a tenth aspect of the present invention, in the seventh aspect, the light source unit may be mounted so as to be slidable with respect to the outer peripheral section.

According to an eleventh aspect of the present invention, in any one of the seventh to tenth aspects, a plurality of light-emitting elements may be arranged side by side in a circumferential direction of the projection section in the outer peripheral section.

According to a twelfth aspect of the present invention, in any one of the seventh to tenth aspects, the light-emitting element may be arranged on a central axis of the projection section such that a light-emitting surface of the light-emitting element faces the tip end side of the outer peripheral section.

DETAILED DESCRIPTION OF THE INVENTION

An embodiment of the present invention will be described with reference to FIGS. 1 to 5.

Figure 1:
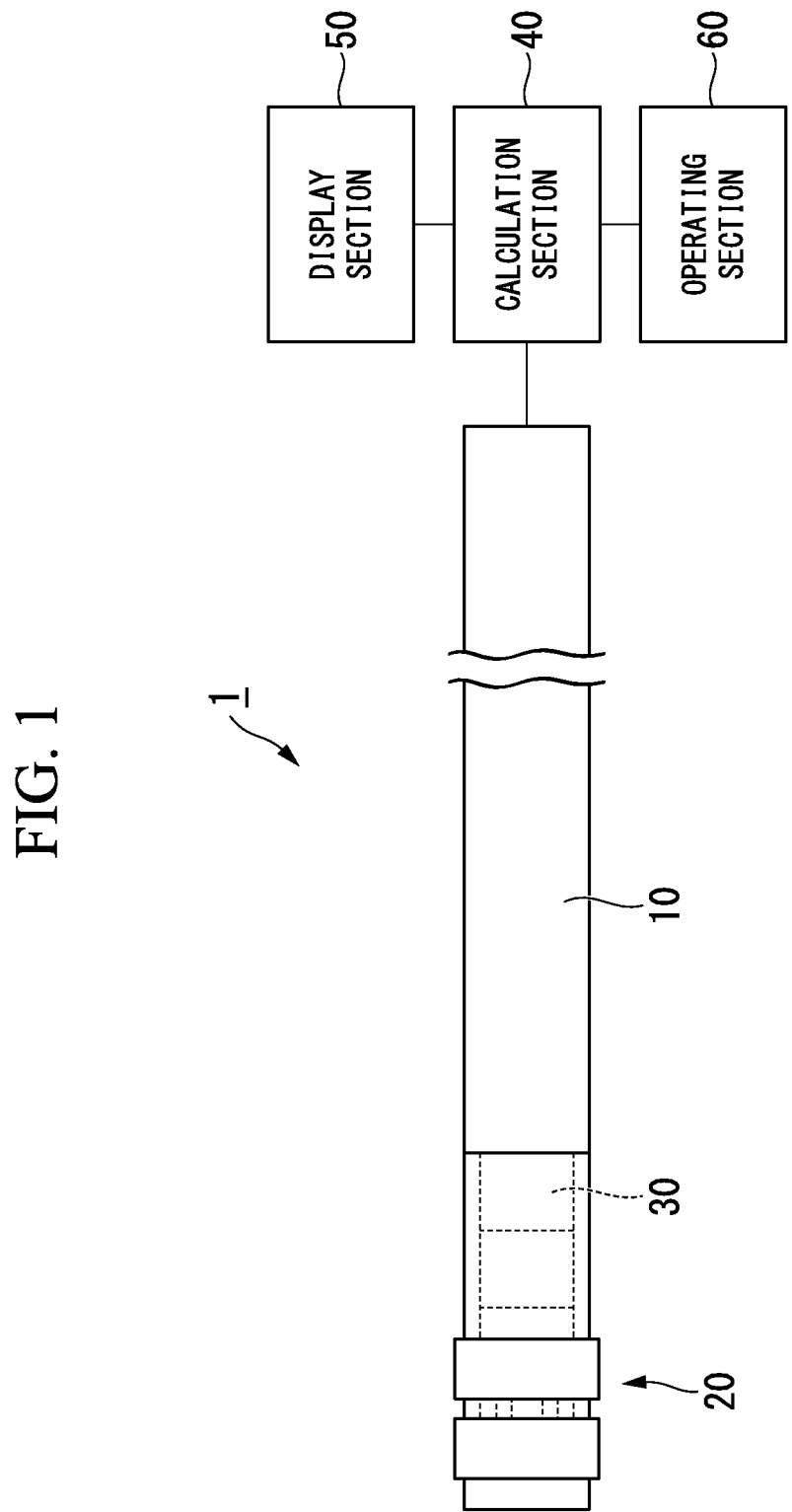
FIG. 1 is a schematic diagram showing the overall configuration of an inner surface shape measuring apparatus according to an embodiment of the present invention.

FIG. 1 is a schematic diagram showing the overall configuration of an inner surface shape measuring apparatus (hereinafter simply referred to as a "measuring apparatus") 1 of this embodiment. The measuring apparatus 1 includes a long insertion section 10, a projection section 20 which is provided on the tip end side of the insertion section 10 and projects a luminous flux having a predetermined thickness (width) T, an imaging section 30 which images a light-section line that is produced by a planar luminous flux, a calculation section 40 which performs processing or analysis of a video signal obtained in the imaging section 30, a display section 50 which displays a picture obtained by the imaging section 30, and an operating section 60 used to perform input of various operations, as shown in FIG. 1. The predetermined thickness T is a dimension of light in the perpendicular direction with respect to a light irradiation direction, as shown in FIG. 2.

The insertion section 10 is formed into a tubular shape and has flexibility except for a certain area on the tip end side. The insertion section may be configured so as to be able to be actively bent by being provided with a known bending mechanism provided with a bending piece, a joint ring, or the like, as necessary.

Figure 2:
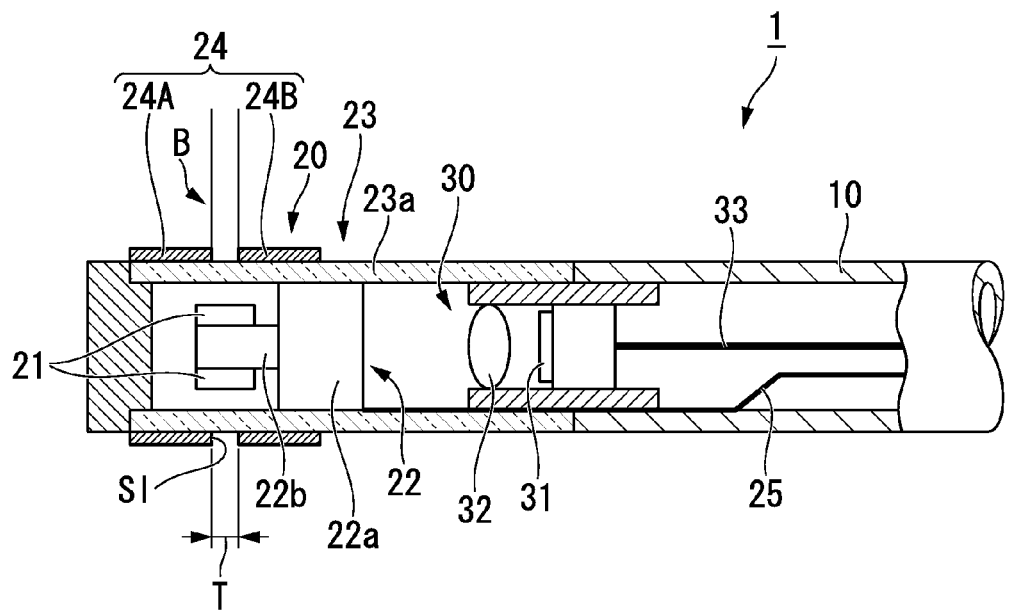
FIG. 2 is a cross-sectional view schematically showing the tip end side of an insertion section of the inner surface shape measuring apparatus.

FIG. 2 is a cross-sectional view schematically showing the tip end side of the insertion section 10. The projection section 20 includes a light source unit 22 having an LED element (a light-emitting element) 21 that is a light source, and an outer peripheral section 23 having a tubular shape and provided on the periphery of the light source unit 22.

The outer peripheral section 23 has a main body 23a formed of resin or the like into a tubular shape and being transparent to allow light to penetrate, and a shielding section 24 mounted so as to be slidable with respect to the main body 23a. The outer diameter of the outer peripheral section 23 is approximately the same as that of the insertion section 10 and a base end portion thereof is connected to a tip end portion of the insertion section 10.

The light source unit 22 has a base 22a and a substrate section 22b connected to the base 22a. A single LED element 21 is mounted on each of the two sides in a thickness direction of the substrate section 22b. Since the substrate section 22b is arranged so as to extend approximately parallel to an axis of the outer peripheral section 23, each LED element 21 is arranged such that its own light-emitting surface faces in a direction approximately orthogonal to the axis of the outer peripheral section 23.

Wiring 25 which supplies electricity to the light source unit 22 extends to the base end side through the inside of the insertion section 10.

The shielding section 24 has a first shielding tube 24A and a second shielding tube 24B having approximately the same shape. The first shielding tube 24A and the second shielding tube 24B are formed of metal, colored resin, or the like and prevent light emitted from the LED elements 21 from leaking out of the outer peripheral section 23. The inner diameters of the first shielding tube 24A and the second shielding tube 24B are slightly larger than the outer diameter of the outer peripheral section 23. For this reason, each of the shielding tubes 24A and 24B fitted to the outside of the outer peripheral section 23 can slide in a direction of an axis of the outer peripheral section 23 with respect to the outer peripheral section 23 and be locked to the outer peripheral section 23 at an arbitrary position by friction locking or the like. Further, the distance between the first shielding tube 24A and the second shielding tube 24B can also be regulated to be an arbitrary value.

An opening on the tip end side of the outer peripheral section 23 is shielded and has a configuration in which neither leak of the light of the light source unit 22 from the opening nor entry of dust or the like into the outer peripheral section 23 occurs. Further, the base end side of the projection section 20 is shielded by the base 22a, and thus the light of the light source unit 22 does not leak even to a space in which the imaging section 30 is arranged.

The imaging section 30 is provided with an imaging element 31 such as a CCD or a CMOS and an imaging optical system 32 and images a disk-shaped luminous flux projected from the projection section 20 and a light-section line which is produced on the inner surface of a tested object according to the luminous flux. A basic structure of the imaging section 30 is known and an imaging section having the same imaging mechanism or the like as that of a general endoscopic device can be used. A lighting mechanism such as an LED element may be provided in the imaging section, as necessary. The imaging element 31 need not be necessarily arranged on the tip end side of the insertion section 10. In a case where the imaging element 31 is arranged on the base end side of the insertion section 10 or in the vicinity of the calculation section 40, it is favorable if the imaging element 31 is connected to a position where a disk-shaped luminous flux or the like can be observed, by an image guide. A video signal obtained in the imaging section 30 is sent to the calculation section 40 through a signal line 33.

As shown in FIG. 1, the calculation section 40 performs processing of a video signal received from the imaging section 30, calculation of the inner surface shape of a tested object based on a light-section line in a picture, or the like. Further, the calculation section 40 controls the overall operation of the measuring apparatus 1 on the basis of operation input from the operating section 60.

The display section 50 displays a video signal processed in the calculation section 40 and a known display or the like can be used.

There is no particular limitation to a specific aspect of the operating section 60, and the specific aspect of the operating section 60 may be a controller provided on the base end side of, for example, the insertion section and may also be a graphical user interface (GUI) such as buttons displayed on the screen of the display section 50, or a keyboard. The specific aspect of the operating section 60 may also be appropriately selected and determined from various known aspects.

An operation at the time of use of the measuring apparatus 1 configured as described above will be described. First, a user moves the first shielding tube 24A and the second shielding tube 24B to a desired position of the outer peripheral section 23 and locks and fixes the first shielding tube 24A and the second shielding tube 24B. Since the gap between a base end of the first shielding tube 24A and a tip end of the second shielding tube 24B becomes a slit 51 and a disk-shaped luminous flux (described later) is projected therethrough, by regulating the position of each of the shielding tubes 24A and 24B in the outer peripheral section 23, it is possible to regulate a projection position of a light-section line and the thickness, the brightness, or the like of the disk-shaped luminous flux. The slit 51 is provided in a circumferential direction of the outer peripheral section 23.

The user inserts the insertion section 10 into a tested object and introduces a tip end portion of the insertion section 10 including the projection section 20 to a target site to perform measurement, while observing the inside of the tested object through the outer peripheral section 23 by the imaging section 30. As lighting at the time of the introduction, a disk-shaped luminous flux which is projected from the projection section 20 may be used and a lighting mechanism separately provided in the imaging section may also be used.

If a tip end of the insertion section 10 reaches the target site, the user turns on the light source unit 22 of the projection section 20 (there is also a case where the light source unit 22 has been already turned on). In this way, light emitted from the LED element 21 penetrates the outer peripheral section 23 which has a transparency, and leaks to the outside of the projection section 20 through the slit 51 formed between the first shielding tube 24A and the second shielding tube 24B. In this way, a substantially disk-shaped luminous flux B is projected from the projection section 20. The disk-shaped luminous flux reaches the inner surface of the tested object and produces a light-section line on the inner surface of the tested object.

The user obtains a picture of the inner surface of the tested object including the light-section line through the outer peripheral section 23 by the imaging section 30. A video signal sent from the imaging section 30 is appropriately processed in the calculation section 40 and displayed on the display section 50. If the user performs predetermined operation input through the operating section 60, known calculation using a light-section method is performed in the calculation section 40 on the basis of an image displayed on the display section 50, and thus the inner surface shape of the tested object is measured.

Since the light emitted from the LED element 21 is not a parallel light, the light slightly diffuses at the outside of the projection section 20. However, when the distance between the tested object and the insertion section 10 is small, the diffusion hardly affects measurement. Further, even in a case where the tested object and the insertion section are away from each other, it is possible to perform measurement by a light-section method with certain accuracy.

According to the measuring apparatus 1 of this embodiment, since the projection section 20 is configured to include the light source unit 22 and the shielding section 24 having simple structures, a conical reflecting mirror processed with a high degree of accuracy is not required. Further, since precise alignment of a conical reflecting mirror and a light source is also not required, a structure to project a disk-shaped luminous flux can be configured inexpensively and easily. In addition, it is also easy to achieve a reduction in the size of the apparatus.

Figure 3:
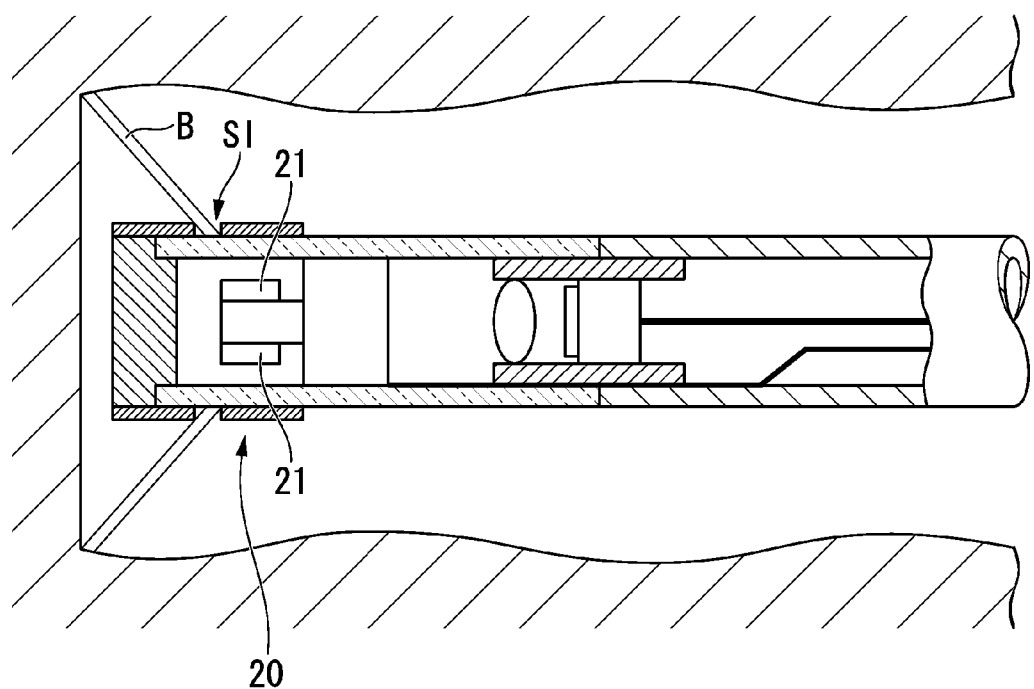
FIG. 3 is a cross-sectional view showing one form at the time of use of the inner surface shape measuring apparatus.

Further, since it is not necessary to dispose a conical reflecting minor on the tip end side of the projection section, it is possible to shorten the length in an axis direction of the projection section. When axially moving the insertion section 10 back and forth, thereby scanning the inner surface of the tested object while projecting a disk-shaped luminous flux onto the tested object, if it is a small-sized projection section, it is possible to reduce an area where the disk-shaped luminous flux cannot be projected, and thus it is possible to expand a measurable area. In addition, as shown in FIG. 3, by making the slit Si through which the disk-shaped luminous flux is projected be located further to the tip end side than the LED element 21, it also becomes possible to project forward the luminous flux B, thereby producing a light-section line further in front than the projection section 20. As a result, it is possible to eliminate an area which cannot be scanned. At this time, the shape of the luminous flux B which is projected from the projection section 20 is the lateral shape of a cone or a truncated cone.

In addition, since the shielding section 24 has the first shielding tube 24A and the second shielding tube 24B, by easily moving and locking the shielding section 24 with respect to the outer peripheral section 23, it is possible to freely and easily regulate the projection position of the luminous flux and the thickness, the brightness, or the like of the luminous flux.

In addition, since the light-emitting surface of the LED element 21 of the light source unit 22 faces in a direction orthogonal to the axis of the outer peripheral section 23, the light emitted from the LED element 21 can be efficiently irradiated toward the outside of the projection section.

Figure 4:
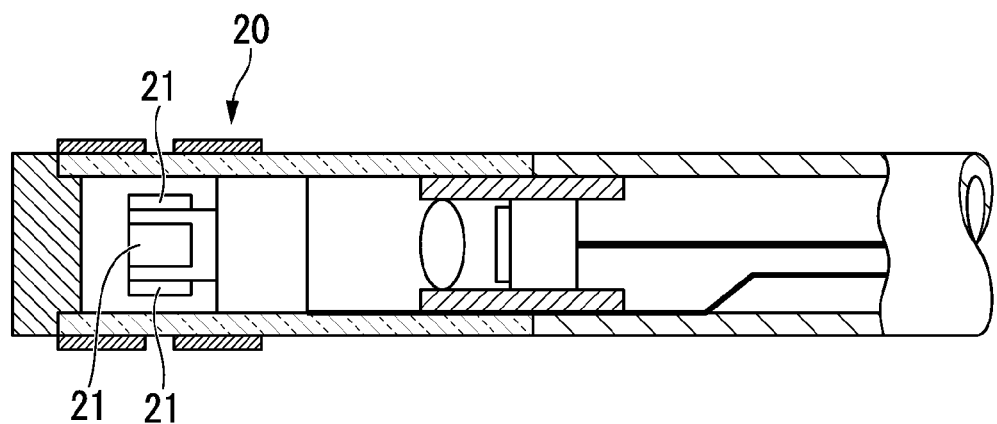
FIG. 4 is a cross-sectional view schematically showing the tip end side of an insertion section in a modified example of the inner surface shape measuring apparatus.
Figure 5:
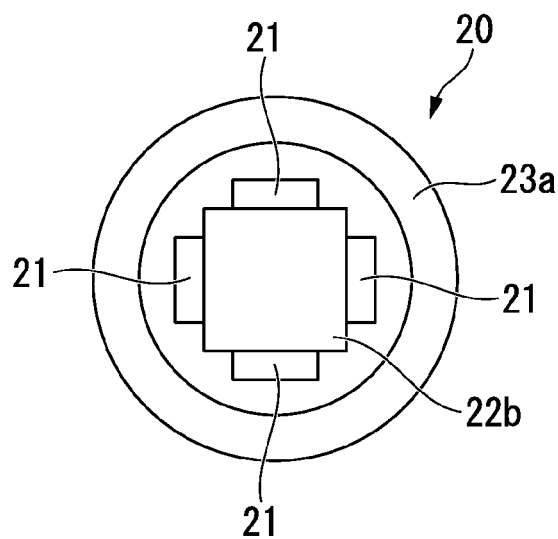
FIG. 5 is a cross-sectional view of a projection section of the modified example.

In this embodiment, an example in which the light source unit is provided with two LED elements has been described. However, the number of light sources of the light source unit is not limited thereto, and for example, as shown in FIGS. 4 and 5, four LED elements 21 may be arranged side by side in a circumferential direction of the projection section 20 in the main body 23a. Then, it is possible to reduce unevenness of brightness of a luminous flux which is projected. Of course, it is also possible to further increase the number of light sources. In addition, a plurality of light sources may be arranged in an array form at some phases in a circumferential direction, for example, and a light source may also be arranged only on one side (for example, the upper side) in the thickness direction of the substrate section 22b. In the latter case, a luminous flux is projected only from an area of the approximately upper half of the projection section 20. However, the projection section 20 and the insertion section 10 are usually in contact with the lower surface of a tested object. Accordingly, even if a luminous flux is not projected to the lower surface side, in many cases, measurement of a large portion of the inner surface of a tested object is possible.

Next, another embodiment of the present invention will be described referring to FIG. 6. A difference between this embodiment and the above embodiment is a disposition aspect of the light source. In the following description, a configuration or the like that has already been previously described is denoted by the same reference numeral and repeated description thereof is omitted here.

Figure 6:
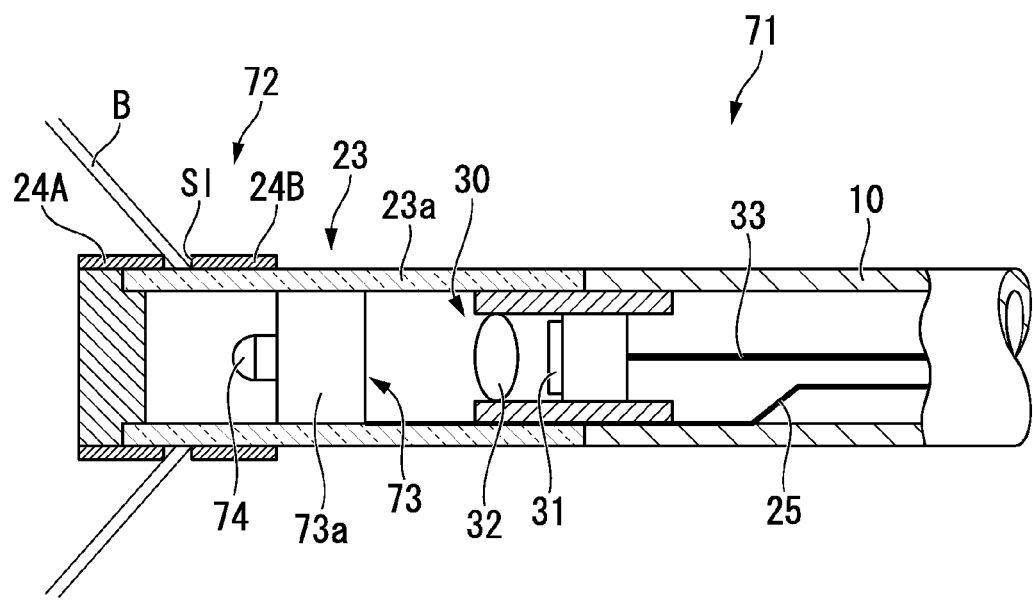
FIG. 6 is a cross-sectional view schematically showing the tip end side of an insertion section of an inner surface shape measuring apparatus according to another embodiment of the present invention.

FIG. 6 is a cross-sectional view schematically showing a tip end portion of a measuring apparatus 71 of this embodiment. In a light source unit 73 of a projection section 72, a base 73a also serves as a substrate section and a single LED element 74 is mounted on the surface on the tip end side of the base 73a. The LED element 74 is arranged on the central axis of the projection section 72 such that the light-emitting surface thereof faces forward in a direction in which the axis of the outer peripheral section 23 extends, and the direction of the light-emitting surface and the axis of the projection section 72 are substantially parallel.

Also in the measuring apparatus 71 of this embodiment, similar to the above embodiment, a structure to project the luminous flux B can be configured inexpensively and easily.

Further, since only one LED element 74 is provided and the light-emitting surface thereof faces forward, it is possible to further reduce the size of the entire apparatus. In the configuration of this embodiment, since intensive light is emitted forward, as shown in FIG. 6, it is suitable to project the luminous flux B further forward than the LED element 74.

This embodiment is a configuration particularly suitable for a reduction in size. However, it is natural that a plurality of light sources may be arranged on the base 73a as far as it is permitted dimensionally.

While preferred embodiments of the present invention have been described and illustrated above, it should be understood that these are exemplary of the present invention and are not to be considered as limiting. Additions, omissions, substitutions, and other modifications can be made without departing from the spirit or scope of the present invention. Accordingly, the present invention is not to be considered as being limited by the foregoing description, and is only limited by the scope of the appended claims.

For example, first, in the measuring apparatus according to the present invention, the configuration of the projection section is not limited to each embodiment described above and can be changed.

Figure 7:
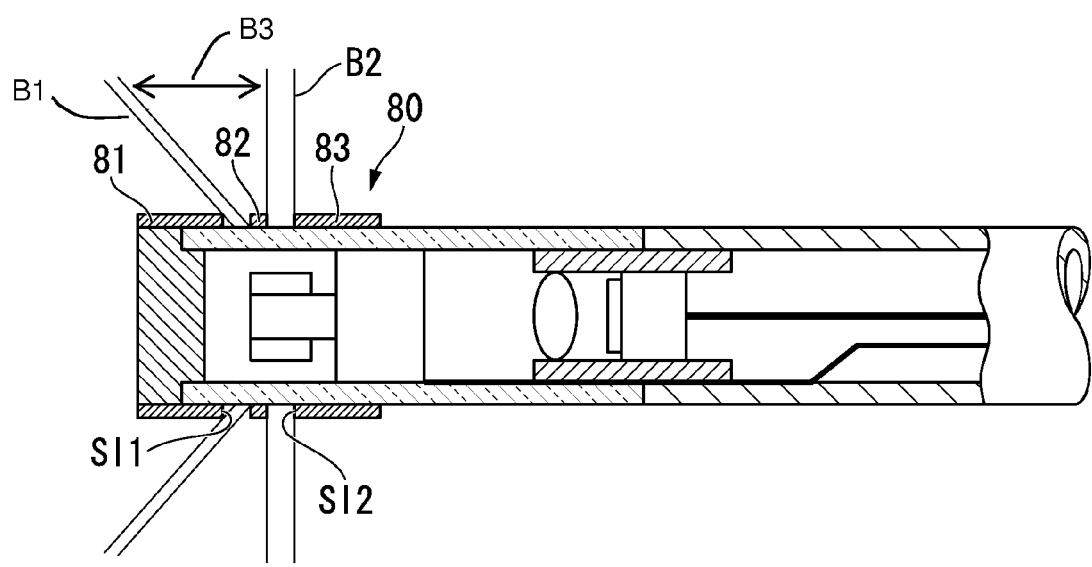
FIG. 7 is a cross-sectional view schematically showing the tip end side of an insertion section of an inner surface shape measuring apparatus according to a modified example of the present invention.

In a modified example shown in FIG. 7, a configuration is made in which a shielding section 80 is provided with three shielding tubes 81, 82, and 83, and slits S11 and S12 are respectively formed between the shielding tube 81 and the shielding tube 82 and between the shielding tube 82 and the shielding tube 83 so as to be able to project two luminous fluxes B1 and B2 with a shadow portion B3 therebetween. Then, a plurality of light-section lines can be produced at a time, and thus it is possible to efficiently perform the measurement of an inner surface shape. If a plurality of shielding tubes in which dimensions in an axis direction are different from each other is prepared, it becomes possible to further increase the number of slits or regulate the width or the positional relationship of each slit to a desired width or positional relationship.

Further, instead of configuring the shielding section by a plurality of shielding tubes, the shielding section may be configured by using a transparent tubular member in which light shielding areas that are not penetrable by light are provided by blackly coloring or the like areas with one or more of ring-shaped transparent areas (slits) left on the transparent tubular member. In the case of such a shielding section, by preparing several types of shielding sections having different slit widths in advance and selectively using it in accordance with a tested object, it is possible to regulate the thickness, the brightness, or the like of a disk-shaped luminous flux. In this manner, even in the shielding section having a configuration in which a plurality of shielding tubes is not used, the same effects can be obtained.

In addition, by using a tubular member having a transparent area and a light shielding area as an outer peripheral section, a projection section may be configured without using a shielding tube or the like. Even in this case, if the positioning in an axial direction of the light source unit is performed by using a jig or the like in a state where the tip end side of the outer peripheral section 23 is opened, and the tip end side of the outer peripheral section 23 is shielded after the positioning, it is possible to easily perform adjustment of the projection position of a light-section line.

Further, the shielding section need not be necessarily fitted to the outside of the outer peripheral section and may be fitted to the inside.

Further, the light-emitting element is also not limited to the LED element described above, and other light-emitting elements such as a laser diode or the like may be used. In addition, light which is emitted from a light-emitting element may be appropriately regulated to a desirable form by combining various optical members such as a diffuser plate or a collimating lens, as necessary.

In addition, by using a driving mechanism such as a motor, the shielding section or the imaging section may be configured so as to be advanceable and retreatable with respect to the insertion section. Then, even after the measuring apparatus is inserted into a tested object, it is possible to perform regulation of a luminous flux which is emitted or an image which is obtained.

Further, as shown in FIG. 7, the measuring apparatus according to the present invention may have a configuration to project the shadow portion B3 having a disk shape or the like with a predetermined width, rather than just a luminous flux having a disk shape or the like, by providing a ring-shaped light shielding area such as the shielding tube 82 in the projection section, or the like. Also in this case, inner surface measurement by a light-section method can be performed with the boundary line between the shadow and light on the surface of a tested object as a light-section line.

What is claimed is:

1. An inner surface shape measuring apparatus that measures an inner surface shape of a tested object by using a light-section method, the measuring apparatus comprising:
   a projection section which includes an outer peripheral section having a tubular shape and having a circumferential slit through which light is penetrable;
   a light source unit which includes a light-emitting element and which is arranged in the outer peripheral section in a vicinity of the slit such that light emitted from the light source unit directly penetrates through the slit, whereby the projection section projects a luminous flux that has a predetermined thickness from the slit onto the tested object; and
   an imaging section which images the inner surface of the tested object with the luminous flux projected thereon.

2. The inner surface shape measuring apparatus according to claim 1, wherein the outer peripheral section includes a transparent tubular main body and a shielding section which is mounted so as to be slidable with respect to the main body, at least a portion of the shielding section having a light shielding property.

3. The inner surface shape measuring apparatus according to claim 2, wherein the shielding section is configured with a plurality of shielding tubes having the light shielding property.

4. The inner surface shape measuring apparatus according to claim 1, wherein:
   at least a portion of the outer peripheral section has a light shielding property; and
   the light source unit is mounted so as to be slidable with respect to the outer peripheral section.

5. The inner surface shape measuring apparatus according to claim 1, wherein a plurality of light-emitting elements is arranged side by side in a circumferential direction of the projection section in the outer peripheral section.

6. The inner surface shape measuring apparatus according to claim 1, wherein the light-emitting element is arranged on a central axis of the projection section such that a light-emitting surface of the light-emitting element faces a tip end side of the outer peripheral section.

7. An inner surface shape measuring apparatus that measures an inner surface shape of a tested object by using a light-section method, the measuring apparatus comprising:
   a projection section which includes an outer peripheral section having a tubular shape and having first and second circumferential slits through which light is penetrable;
   a light source unit which includes a light-emitting element and which is arranged in the outer peripheral section in a vicinity of the first and second slits such that light emitted from the light source unit directly penetrates through the slits, whereby the projection section projects two luminous fluxes with a shadow therebetween that has a predetermined thickness onto the tested object; and an imaging section which images the inner surface of the tested object with the shadow projected thereon.

8. The inner surface shape measuring apparatus according to claim 7, wherein the outer peripheral section includes a transparent tubular main body and a light shielding section mounted so as to be slidable with respect to the main body, the light shielding section having a light shielding property and inducing the shadow in between the first and second slits.

9. The inner surface shape measuring apparatus according to claim 8, wherein the light shielding section comprises a plurality of shielding tubes having the light shielding property.

10. The inner surface shape measuring apparatus according to claim 7, wherein the light source unit is mounted so as to be slidable with respect to the outer peripheral section.

11. The inner surface shape measuring apparatus according to claim 7, wherein a plurality of light-emitting elements is arranged side by side in a circumferential direction of the projection section in the outer peripheral section.

12. The inner surface shape measuring apparatus according to claim 7, wherein the light-emitting element is arranged on a central axis of the projection section such that a light-emitting surface of the light-emitting element faces a tip end side of the outer peripheral section.

* * * * *